US009629794B2

(12) United States Patent
Kaur et al.

(10) Patent No.: US 9,629,794 B2
(45) Date of Patent: Apr. 25, 2017

(54) COMPOSITIONS COMPRISING AN NFκB-INHIBITOR AND A TROPOELASTIN PROMOTER

(71) Applicant: JOHNSON & JOHNSON CONSUMER INC., Skillman, NJ (US)

(72) Inventors: Simarna Kaur, Watchung, NJ (US); Michael Southall, Pennington, NJ (US); Samantha Tucker-Samaras, Long Valley, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 262 days.

(21) Appl. No.: 14/493,871

(22) Filed: Sep. 23, 2014

(65) Prior Publication Data

US 2015/0064292 A1    Mar. 5, 2015

Related U.S. Application Data

(62) Division of application No. 12/572,545, filed on Oct. 2, 2009, now abandoned.

(51) Int. Cl.
*A61K 36/00* (2006.01)
*A61K 8/97* (2017.01)
*A61K 8/34* (2006.01)
*A61K 8/35* (2006.01)
*A61K 8/46* (2006.01)
*A61Q 19/08* (2006.01)

(52) U.S. Cl.
CPC ............... *A61K 8/97* (2013.01); *A61K 8/347* (2013.01); *A61K 8/35* (2013.01); *A61K 8/466* (2013.01); *A61Q 19/08* (2013.01)

(58) Field of Classification Search
None
See application file for complete search history.

(56) References Cited

U.S. PATENT DOCUMENTS

| | | |
|---|---|---|
| 1,649,670 A | 11/1927 | Dohme et al. |
| 2,697,118 A | 12/1954 | Lundsted et al. |
| 3,193,507 A | 7/1965 | Jacobs |
| 4,093,667 A | 6/1978 | Starks |
| 4,337,370 A | 6/1982 | Takisawa et al. |
| 4,959,393 A | 9/1990 | Torihara et al. |
| 5,227,459 A | 7/1993 | Pawelek et al. |
| 5,384,116 A | 1/1995 | Pawelek et al. |
| 5,618,519 A | 4/1997 | Pawelek et al. |
| 5,705,145 A | 1/1998 | Miklean et al. |
| 6,797,697 B2 | 9/2004 | Seiberg et al. |
| 6,852,310 B2 | 2/2005 | Harichian et al. |
| 6,863,897 B2 | 3/2005 | Love et al. |
| 6,869,598 B2 | 3/2005 | Love et al. |
| 6,926,886 B2 | 8/2005 | Lin et al. |
| 7,025,951 B2 | 4/2006 | Seiberg et al. |
| 7,214,655 B2 | 5/2007 | Seiberg et al. |
| 7,468,464 B2 | 12/2008 | Harichian et al. |
| 8,084,504 B2 | 12/2011 | Johnson et al. |
| 8,318,217 B2 | 11/2012 | Kaur et al. |
| 8,425,941 B2 | 4/2013 | Yagi et al. |
| 2002/0182166 A1 | 12/2002 | Martin et al. |
| 2003/0003170 A1 | 1/2003 | Callaghan et al. |
| 2004/0109832 A1 | 6/2004 | Harichian et al. |
| 2004/0156873 A1 | 8/2004 | Gupta |
| 2005/0048008 A1 | 3/2005 | Gupta |
| 2006/0019002 A1 | 1/2006 | Xue |
| 2006/0088608 A1 | 4/2006 | Seiberg et al. |
| 2006/0120975 A1 | 6/2006 | Scherl et al. |
| 2006/0210497 A1 | 9/2006 | Harichian et al. |
| 2006/0239945 A1 | 10/2006 | Bapat et al. |
| 2006/0264497 A1 | 11/2006 | Zeligs |
| 2006/0269504 A1 | 11/2006 | James |
| 2006/0292184 A1 | 12/2006 | Richardson et al. |
| 2007/0003536 A1 | 1/2007 | Zimmerman et al. |
| 2007/0042010 A1 | 2/2007 | Southall et al. |
| 2007/0098655 A1 | 5/2007 | Schmaus et al. |
| 2007/0184017 A1 | 8/2007 | Faryniarz et al. |
| 2007/0196523 A1 | 8/2007 | Koganov |
| 2008/0026974 A1 | 1/2008 | Barnhart et al. |
| 2008/0095719 A1* | 4/2008 | Herrmann ............... A61K 8/97 424/48 |
| 2008/0131382 A1 | 6/2008 | Harichian et al. |
| 2008/0249029 A1 | 10/2008 | Shapiro et al. |
| 2008/0260671 A1 | 10/2008 | De La Torre et al. |
| 2008/0286217 A1 | 11/2008 | Chaudhuri |
| 2008/0305059 A1 | 12/2008 | Chaudhuri |
| 2008/0317887 A1 | 12/2008 | Mitchell et al. |
| 2009/0087395 A1 | 4/2009 | Lin et al. |
| 2010/0124539 A1 | 5/2010 | Hanson |

(Continued)

FOREIGN PATENT DOCUMENTS

| | | |
|---|---|---|
| CN | 102573820 A | 7/2012 |
| DE | 101 18 894 A1 | 10/2002 |

(Continued)

OTHER PUBLICATIONS

Colipa Guideline: Guideline for the Colorimetric Determination of Skin Colour Typing and Prediction of the Minimal Erythemal Dose (Med) Without UV Exposure, published in 2007.
*International Cosmetic Ingredient Dictionary and Handbook*, eds. Pepe, Wenninger and McEwen, (The Cosmetic, Toiletry, and Fragrance Assoc., Washington, D.C., 9th Edition, 2002), pp. 2930-2936; pp. 2962-2971; pp. 2979-2984.
Kolbe et al.; "4-n-butylresorcinol, a highly effective tyrosinase inhibitor for the topical treatment of hyperpigmentation"; 2013; Journal of the European Academy of Dermatology and Venereology; 27 (Suppl. 1): 19-23.
Kaur et al., "4-Hexyl-1,3-phenylenediol, a nuclear factor-kB inhibitor, improves photodamaged skin and clinical signs of ageing in a double blinded, randomized controlled trial"; 2015; British Journal of Dermatology; 173: 218-226.
EP Search Report for Application No. EP 15161428 dated Oct. 6, 2015.

(Continued)

*Primary Examiner* — Qiuwen Mi

(57) ABSTRACT

The present invention relates to a composition comprising an NFκB-inhibitor and a tropoelastin promoter, and methods of treating signs of skin aging using said compositions.

3 Claims, No Drawings

(56) References Cited

U.S. PATENT DOCUMENTS

| | | | |
|---|---|---|---|
| 2010/0189669 A1 | 7/2010 | Hakozaki | |
| 2010/0291014 A1 | 11/2010 | Tellefsen et al. | |
| 2011/0081305 A1 | 4/2011 | Cochran et al. | |
| 2011/0081430 A1 | 4/2011 | Kaur et al. | |
| 2011/0081431 A1 | 4/2011 | Kaur et al. | |
| 2011/0081433 A1 | 4/2011 | Kaur et al. | |
| 2011/0171288 A1 | 7/2011 | Mohammadi et al. | |
| 2012/0064149 A1 | 3/2012 | Johnson et al. | |
| 2012/0128605 A1 | 5/2012 | Cochran et al. | |
| 2012/0128613 A1 | 5/2012 | Cochran et al. | |
| 2012/0177587 A1 | 7/2012 | Daubresse et al. | |
| 2013/0071453 A1 | 3/2013 | Sojka | |
| 2013/0162992 A1 | 6/2013 | Schmidt et al. | |
| 2013/0164393 A1 | 6/2013 | Kaur et al. | |
| 2013/0165512 A1 | 6/2013 | Oddos | |
| 2013/0202546 A1 | 8/2013 | Howell | |
| 2014/0086859 A1 | 3/2014 | Dufort et al. | |
| 2015/0272837 A1 | 10/2015 | Brillouet et al. | |

FOREIGN PATENT DOCUMENTS

| | | | |
|---|---|---|---|
| DE | 10157490 A1 | 6/2003 | |
| EP | 1 250 908 A2 | 10/2002 | |
| EP | 1 299 069 B1 | 12/2005 | |
| EP | 1 974 773 A2 | 10/2008 | |
| EP | 1 987 811 A1 | 11/2008 | |
| EP | 2 036 565 A1 | 3/2009 | |
| EP | 2 045 297 A2 | 4/2009 | |
| EP | 2 100 593 A1 | 9/2009 | |
| EP | 2674146 | 12/2013 | |
| FR | 2 746 008 A1 | 9/1997 | |
| GB | 821726 | 10/1959 | |
| GB | 2438999 A | 12/2007 | |
| IN | 188649 B | * 10/2002 | |
| JP | 11100324 | 4/1999 | |
| JP | 2000-327557 A | 11/2000 | |
| JP | 4004182 B2 | 11/2000 | |
| JP | 2001 302505 A | 10/2001 | |
| JP | 2004-107210 A | 4/2004 | |
| JP | 2006-327965 A | 12/2006 | |
| JP | 2007254412 A | * 10/2007 | |
| JP | 2007332116 | 12/2007 | |
| JP | 2008-184431 A | 8/2008 | |
| JP | 2009084164 A | 4/2009 | |
| KR | 2003089598 A | 11/2003 | |
| WO | WO 98/53822 A1 | 12/1998 | |
| WO | WO 02/074280 A1 | 9/2002 | |
| WO | WO 03/080009 A1 | 10/2003 | |
| WO | WO 03/082231 A2 | 10/2003 | |
| WO | WO 2004/052330 A1 | 6/2004 | |
| WO | WO 2004/062637 A1 | 7/2004 | |
| WO | WO 2004/105736 A1 | 12/2004 | |
| WO | WO 2006/097223 A1 | 9/2006 | |
| WO | WO 2006/128032 A2 | 11/2006 | |
| WO | WO 2007/021240 A1 | 2/2007 | |
| WO | WO 2008/143761 A1 | 11/2008 | |
| WO | WO 2008/148016 A1 | 12/2008 | |
| WO | WO 2008/153629 | 12/2008 | |
| WO | WO 2009/067095 A1 | 5/2009 | |
| WO | WO 2009/145300 A1 | 12/2009 | |

OTHER PUBLICATIONS

Prakash et al., "Multifunctional Ingredients: the novel face of natural" Antiaging: physiology to formulation (2006), pp. 181-188.
Belikov, V.G., "Pharmaceutical Chemistry", M. Higher School, 1993, vol. 1, pp. 43-47.
U.S. Appl. No. 12/869,250, filed Oct. 1, 2010, Kaur et al.
U.S. Appl. No. 61/247,992, filed Oct. 2, 2009, Southall et al.
U.S. Appl. No. 13/775,959, filed Feb. 25, 2013, Southall et al.
U.S. Appl. No. 12/572,545, filed Oct. 2, 2009, Southall et al.
U.S. Appl. No. 13/779,814, filed Feb. 28, 2013, Southall et al.
U.S. Appl. No. 12/572,565, filed Oct. 2, 2009, Southall et al.
U.S. Appl. No. 13/298,816, filed Nov. 17, 2011, Johnson et al.
U.S. Appl. No. 13/779,854, filed Feb. 28, 2013, Southall et al.
U.S. Appl. No. 12/572,377, filed Oct. 2, 2009, Southall et al.
U.S. Appl. No. 13/362,338, filed Jan. 31, 2012, Southall et al.
U.S. Appl. No. 13/362,367, filed Jan. 31, 2012, Southall et al.
U.S. Appl. No. 12/572,650, filed Oct. 2, 2009, Southall et al.
U.S. Appl. No. 14/227,260, filed Mar. 27, 2014, Brillouet et al.
Int'l. Search Report for Application No. PCT/US2010/051080, dated Dec. 6, 2010.
EP Search Report for Application No. EP 10251712.5 dated May 6, 2011.
EP Search Report for Application No. 10 25 1715 dated Apr. 11, 2013.
EP Search Report for Application No. 10 25 1717 dated Apr. 9, 2013.
Database GNPD [Online] Mintel; May 2008, "Anti-oxidant Bio Moisturizing Cream SPF 15", XP002695056, Database accession No. 914469.
Database GNPD [Online] Mintel; Jan. 2004, "Max Strength Sore Throat Relief Lozenges", XP002695248, Database accession No. 252009.
Database WPI Week 200849, Thomson Scientific, London, GB; AN2008-H65100, XP002695249, & JP 2007 254412 A (Kuraray Co Ltd.) Oct. 4, 2007, Abstract.
Database WPI Week 199637 Thomson Scientific, London, GB; AN1996-368117, XP002625251, & JP H08 176004 A (Lion Corp) Jul. 9, 1996, Abstract.
Database GNPD [Online] Mintel: Oct. 2008, "Eye Recovery", XP002695054, Database accession No. 992121.
Database GNPD [Online] Mintel: Mar. 2009, "Facial Serum", XP002695055, Database accession No. 1076327.
Database GNPD [Online] Mintel; Jun. 2009, "Instant Facial Sculpting", Database accession No. 1123303.
Database GNPD [Online] Mintel; Feb. 2009, Advanced Luminescence Serum), Database accession No. 1060752.
Suzuki Y. J. et al., "Inhibition of NF-kappaB Activation by Vitamin E Derivatives", Biochemical and Biophysical Research Communications, vol. 193, No. 1, May 28, 1993, pp. 277-283, XP024767607, Academic Press Inc. Orlando, FL, US, ISSN: 0006-291X, DOI: 10.1006/BBRC.1993.1620.
Staal F. J. et al., "Antioxidants Inhibit Stimulation of HIV Transcription", Aids Research and Human Retroviruses, vol. 9, No. 4, Jan. 1, 1993, pp. 299-306, XP002037900, Mary Ann Liebert, US ISSN: 0889-2229.
*International Cosmetic Ingredient Dictionary and Handbook*, eds. Pepe, Wenninger and McEwen, (The Cosmetic, Toiletry, and Fragrance Assoc., Washington, D.C., 9th Edition, 2002), pp. 2930-36; pp. 2962-2971; pp. 2979-2984.
Bobin, M., et al. "Effects of Color Adjuvants on the Tanning Effect of Dihydroxyacetone", J. Soc. Cosmetology Chemistry, vol. 35, pp. 265-272 (1984).
Cenizo, et al., "LOXL as a Target to Increase the Elastin Content in Adult Skin: A Dill Extract Induces the LOXL Gene Expression," Experimental Dermatology; 2006, vol. 15(8), 574-581.
Database WPI, Week 200223, Thomson Scientific, London, GB; AN 2002-174418 XP002635474, JP 2001 30205A (Kurarray Co Ltd) Oct. 31, 2001, Abstract.
Database WPI, Week 200849, Thomson Scientific, London, GB; AN 2008-H65100 XP002635473, JP 2007 254412 A (Kurarray Co Ltd) Oct. 4, 2007, Abstract.
Database WPI, Week 200930, Thomson Scientific, London, GB; AN 2009-H70662 XP 002635472, JP 2009 084164 A (Septem Soken KK) Apr. 23, 2009, Abstract.
Fukuda et al., Inhibition by Parthenolide of Phorbol Ester-induced Transcriptional Activation of Inducible Nitric Oxide Synthase Gene in a Human Monocyte Cell Line THP-1, Biochemical Pharmacology, (Aug. 15, 2000), vol. 60, No. 4, pp. 595-600.
Hall et al.; "The Solubilization of Hexylresorcinol by an Anionic-Nonionic Surfactant Mixture"; 1966; Ameri. Jour. Pharm.; 138(6): 245-8.
Hamamoto, et al., "Inhibitory effect of azelastine, a potent antiallergic agent, on release of tumor necrosis factor-a from activated human peripheral blood mononuclear cells and U937 cells," Exp Dermatol, 1993: 2: p. 231-235.

(56) References Cited

OTHER PUBLICATIONS

Herrmann, et al., "Blackberry Leaf Extract A New Anti-Aging Active," SOFW Journal; 2006, vol. 132(4), 42-46.
Lamaison, et al., "Tannin Content and Elastase Inhibiting Activity in the Rosaceae Family," Ann. Pharmaceutiques Francaises; 1990, vol. 48, 335-340.
Lin et al., "Theaflavin-3,3'-digallate from black tea blocks the nitric oxide synthase by down-regulating the activation of NF-kB in macrophages," European Journal of Pharmacology, vol. 367, No. 2-3, Feb 1999, p. 379-388, XP009090023.
Liu, R. et al., "Retinoic Acid Increases Elastin in Neonatal Rat Lung Fibroblast Cultures," Am. Physiol, Society, 1993, 265(5pt. 1):L430-437.
Liu, X. et al., "Elastic Fiber Homeostasis Requires Lysyl Oxidase-like 1 Protein," Nature Genetics ; 2004, vol. 36(2), 178-182.
Ochsner et al.; "Prediction of Solubility in Nonideal Multicomponent Systems Using the UNIFAC Group Contribution Model"; 1985; Journal of Pharmaceutical Sciences; 74(6): 634-637.
Xia et al.; "Dehydration of ethyl acetate-water mixtures using PVA/ceramic composite pervaporation membrane"; 2011; Separation and Purification Technology; 77:53-59.

\* cited by examiner

COMPOSITIONS COMPRISING AN NFκB-INHIBITOR AND A TROPOELASTIN PROMOTER

CROSS-REFERENCE TO RELATED APPLICATIONS

This application is a divisional of U.S. patent application Ser. No. 12/572,545 filed Oct. 2, 2009, the disclosure of which is hereby incorporated by reference in its entirety.

FIELD OF THE INVENTION

A composition comprising an NFκB-inhibitor and a tropoelastin promoter is provided. The composition is useful, for example, for topical application to the skin.

BACKGROUND OF THE INVENTION

The aging of skin may be understood as being influenced by intrinsic factors and extrinsic factors. Intrinsic factors include natural changes to the skin, which are regulated by genetic makeup. Extrinsic factors include exogenous influences such as UV damage, environmental factors, and the like.

Aging of the skin can adversely affect elasticity and strength of the skin through changes in the two main constituents of the dermal extracellular matrix, the fibrous proteins collagen and elastin. For example, elastin is a large fibrous protein formed by the crosslinking of elastin precursor protein molecules (e.g., tropoelastin) into spiral filaments. Collagen, more ubiquitous than elastin, is another fibrous protein that forms the structural network of skin.

Certain agents are known for their beneficial effect of inhibiting the degradation of crosslinked elastin. For example, it is known that matrix metalloproteinases (MMPs), a group of enzymes that are able to break down the macromolecules in the extracellular matrix, play an important role in elastin degradation. A number of plant extracts have been described as inhibitors of various MMPs. For instance, J. L. Lamaison describes the inhibition of elastase (porcine pancreatic elastase) with extracts of plants selected from the rosaceae group and attributes the inhibition to the tannins they contain. *Ann. Pharmaceutiques Francaises* 1990, 48, 335-340. M. Herrmann et al. disclose that Sym-Matrix, a hydroalcoholic blackberry leaf extract, exhibits the MMP-1, MMP-2, and MMP-9 inhibitory activity. *SOFW Journal* (2006), 132(4), 42-46.

In addition, certain natural or synthetic compounds are known for the beneficial effect of promoting the production of elastin precursor and/or promoting the formation of collagen. For example, retinoids up-regulate elastin production in fibroblasts. Liu et al., *Am J Physiol*. November 1993; 265(5 Pt 1):L430-437. Retinoids are also known to promote collagen formation.

Furthermore, it has also been noted that certain agents positively influence the cross-linking of tropoelastin. For example, lysyl oxidase serves as a crosslinking enzyme and an element of the scaffold to ensure spatially defined deposition of elastin. Liu et al., *Nature Genetics* (2004), 36(2), 178-182. Valerie et al. disclose a dill extract that induces the lysyl oxidase (LOXL) gene expression, which is responsible for elastin cross-linking in adults. *Experimental Dermatology* (2006), 15(8), 574-81. Additionally, currant, cardamon, black radish, box holly, Asea foetida gum, ethyl hexenoate, methyl butyrate, and ethyl decadienoate are disclosed as promoters of LOXL gene expression. GB 2,438,999.

Thus, numerous pathways and agents have been proposed to positively influence elastin and collagen, and skin-properties related thereto. However, the inventors have recognized a need for new agents and combinations of agents that can further positively influence either elastin or collagen, or preferably both.

The inventors have now surprisingly discovered surprising benefits of a particular class of anti-inflammatory compounds, agents that inhibit the cell transcription factor nuclear kappa-B (NFκB). The inventors have found that while NFκB-inhibitors do not themselves necessarily enhance tropoelastin activity, when NFκB-inhibitors are combined with tropoelastin promoters, the resulting combinations exhibit a surprisingly large, unexpected and synergistic boost in tropoelastin promotion efficacy. Even more surprisingly, the inventors have identified certain compounds such as resorcinol derivatives, previously unknown for their inhibitory activity on NFκB, as particularly suitable to dramatically boost the tropoelastin activity of tropoelastin promoters.

SUMMARY OF THE INVENTION

In one aspect, the invention provides a composition comprising an NFκB-inhibitor and a tropoelastin promoter.

According to another aspect, the invention provides a method of treating a sign of skin aging, comprising topically applying to skin in need of such treatment a composition comprising an NFκB-inhibitor and a tropoelastin promoter.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Products described herein may optionally be in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin to treat the signs of skin aging as discussed infra. Such instructions may be printed on the container, label insert, or on any additional packaging.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

Compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

NFκB-INHIBITOR

Compositions of the present invention include an NFκB-inhibitor. As used herein, "NFκB-inhibitor" means a compound that inhibits the cell transcription factor nuclear kappa-B (NFκB). In one embodiment, the NFκB-inhibitor, when tested according to the NFκB-INHIBITION TEST as defined below, has a Percent NFκB Inhibition of at least about 35%, preferably at least about 55%, more preferably at least about 70%, most preferably at least about 90%, when tested at a concentration that is preferably from 1 microgram per milliliter to about 100 micrograms per milliliter. That is, the compound demonstrates the recited Percent NFκB Inhibition at at least one concentration in the range of 1 microgram per milliliter to 100 micrograms per milliliter. The compound need not provide the recited Percent NFκB Inhibition at all concentrations from 1 microgram per milliliter to 100 micrograms per milliliter, but provides the recited Percent NFκB Inhibition at at least one concentration in this range.

In a preferred embodiment, the NFκB-inhibitor has a Percent NFκB Inhibition of at least about 35%, preferably at least about 55%, more preferably at least about 70%, most preferably at least about 90%, when tested at a concentration of 10 micrograms per milliliter.

The NFκB-INHIBITION TEST is conducted in the following manner. FB293 cells, a stable transfected human epithelial cell line containing the gene reporter for NF-kB are used. They may be obtained from, e.g., Panomics (Fremont, Calif.). FB293 are plated at a density of 5×10$^4$ cells/mL in a suitable medium, e.g., Dulbecco's modified Eagle's medium (DMEM) supplemented with 10% fetal bovine serum (Invitrogen, San Diego, Calif.). The FB293 cells are stimulated with 100 ng/mL of Tumor Necrosis Factor-α (TNFα, available from Sigma-Aldrich of St Louis, Mo.) in the presence of the test sample. Separately, a control sample is tested wherein no test sample is applied. Following a 24-hour incubation at 37° C. with 5% $CO_2$, cells are lysed with 40 µl of reporter lysis buffer (Promega, Madison, Wis.). A 20-µl aliquot of the lysate is assayed using a luciferase assay kit (Promega) and counted for 10 s in a Lmax luminometer (Molecular Devices, Sunnyvale, Calif.) with the data represented as the relative light unit/second. Percent NFκB Inhibition of the test sample is calculated as:

$$\text{NFκB Inhibition} = [1-(L_{sample}/L_{control})]*100$$

where $L_{sample}$ is the luminescence of the sample and $L_{control}$ is the luminescence of the control.

The NFκB-inhibitor may be present in the inventive composition in any suitable amount, such as from about 0.01% by weight to about 100% by weight, preferably from about 0.1% to about 20%, more preferably from about 0.1% to about 5%, even more preferably from about 0.2% to about 2%.

In one embodiment, the NFκB-inhibitor is selected from a group consisting of the following compounds: substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), and combinations thereof.

In a preferred embodiment, the NFκB-inhibitor is a substituted resorcinol. Resorcinol is a dihydroxy phenol compound (i.e., 1,3 dihydroxybenzene) having by the following structure:

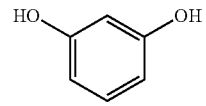

As used herein, "substituted resorcinol" means resorcinol comprising at least one substituent in the 2, 4, 5, or 6 position. Thus, the substituted resorcinol may have as few as one and as many as four substituents. Positions 1 and 3 of the substituted resorcinol comprise —OH groups, as shown above.

It is highly preferred that all of the substituents of the substituted resourcinol are free of phenyl (—$C_6H_5$ aromatic) moieties. In certain embodiments, all of the substituents are free of aromatic moieties (with or without heteroatoms).

In another embodiment, it is preferred that all of the substituents of the substituted resorcinol are free of ketone functionalities (carbonyls bonded to two other carbon atoms).

In certain preferred embodiments, all of the substituents of the substituted resorcinol are free of both phenyl functionalities and ketone functionalities.

In certain preferred embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms. In certain other embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an akyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols include 4-hexyl resorcinol and 4-octylresorcinol, particularly 4-hexyl resorcinol. The structures of 4-hexylresorcinol and 4-octylresorcinol are shown below:

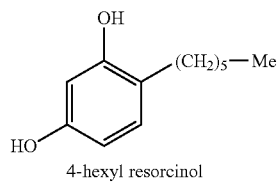

4-hexyl resorcinol

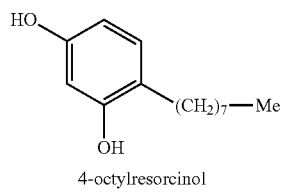

4-octylresorcinol

4-Hexyl resorcinol is commercially available as "SYN-OVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

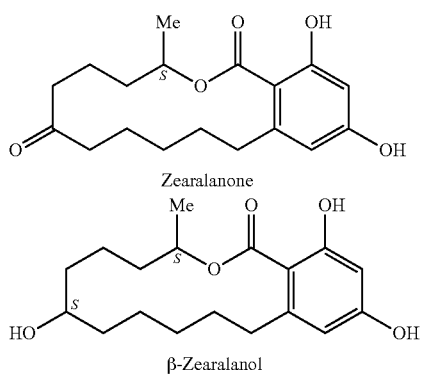

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N=O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

The substituted resorcinol is present in the composition in a safe and effective amount, such as from about 0.01% to about 10%, preferably from about 0.1% to about 5%, more preferably from about 0.2% to about 2%, even more preferably from about 0.5% to about 1.5%, by weight of the composition.

Tropoelastin Promoter

"Tropoelastin promoter," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Suitable tropoelastin promoters may be determined, for example, using the TROPOELASTIN PROMOTER ASSAY. The TROPOELASTIN PROMOTER ASSAY is performed as follows. Rat cardiac myoblasts H9C2 (which may be purchased, for example from ATCC of Manassas, Va.) are used. Cultures are maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 ug/ml streptomycin (Invitrogen Life Technologies, Carlsbad, Calif.). Cell cultures are transiently transfected with the elastin promoter-luciferase reporter construct (Elp2.2, a 2.2 kb elastin promoter fragment from nt −2267 to nt +2, driving the firefly luciferase gene, which may be obtained from Promega, Madison Wis.). DNA is prepared by Qiagen Maxi columns (Qiagen Valencia, Calif.). In all transfections, a construct with the thymidine kinase promoter and the Renilla luciferase reporter gene (PERL-TK, Promega, Madison Wis.) is included as an internal control. Typically, cells grown in 48-well plates are transfected with 0.45 ug total DNA per well using Lipofectamine 2000 (Invitrogen Life Technologies, Carlsbad, Calif.). One day after transfection, cells are treated with agents at indicated concentrations for approximately 24 hours before they are lysed for luciferase assays, using Dual-Luciferase Reporter System from Promega (Madison, Wis.), following manufacturer's protocol. The firefly luciferase activity is measured first (representing elastin promoter activity), followed by the renilla luciferase (internal control), using luminometer LMAX, from Molecular Devices (Sunnyvale, Calif.). The ratio of these two luciferase activities (RLU) is used to evaluate the Tropoelastin Promoter Activity.

The tropoelastin promoter preferably has a Tropoelastin Promoter Activity of at least 1.1, preferably at least 1.25, more preferably at least 1.3, and most preferably at least 1.5, at at least one concentration in the range of 0.5 micrograms/milliliter to 2.5 milligrams per milliliter (on an actives basis), and preferably at at least one concentration in the range of 1.0 micrograms/milliliter to 2.5 milligrams per milliliter (on an actives basis).

While it is contemplated that the NFκB-inhibitor and the tropoelastin promoter may be one and the same compound, molecule, or functional group, in a preferred embodiment, the NFκB-inhibitor and the tropoelastin promoter are two separate and distinct compounds.

Examples of suitable tropoelastin promoters include, but are not limited to, blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "cotinus extract," it is meant an extract of the leaves of "*Cotinus coggygria*," such as a water extract thereof, available from Bilkokoop of Sofia, Bulgaria.

By "feverfew extract," it is meant an extract of the plant "*Tanacetum parthenium*," such as may be produced according to the details set for the in US Patent Application Publication No. 2007/0196523, entitled, "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract.

The extraction process may include by physically removing a piece of such plant, and, for example, grinding it. Further extraction of suitable compounds may also be isolated from the plant by using extraction procedures well known in the art (e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide).

For example, a blackberry leaf extract may be prepared by an extraction with water, alcohols such as ethanol or combination thereof as the solvent. However, an extract produced with a solvent including both ethanol and water is preferred.

The blackberry leaves are preferably dried prior to extraction. It is also preferable to use only the leaves of the blackberry plant for the extraction and not also other plant parts such as the fruit (berries) of the blackberry or its branches and roots.

In one embodiment, the extraction process for the production of a blackberry leaf extract comprises the following steps: a) addition to blackberry leaves of an solvent containing an alcohol selected from the group consisting of methanol, ethanol, n-propanol, isopropanol, b) Extraction of the blackberry leaves with the solvent for up to 72 hours.

Detailed procedures for preparing a suitable blackberry leaf extract are disclosed in US Patent Application Publication No. 2008/0095719, the disclosure of which is incorporated herein in its entirety.

One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name "SymMatrix."

Extracts of "*Phyllanthus niruri*" may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev. Preferably, a low molecular weight fraction of *Phyllanthus niruri* is used, for instance a fraction of *Phyllanthus niruri* substantially free of molecular species having a molecular weight of greater than about 100,000 daltons. Preferably, such low molecular weight fraction is water extractable from the *Phyllanthus niruri* plant.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

The ratio of the concentration of NFκB-inhibitor to the concentration of the tropoelastin promoter in the composition may be varied according to the desired effectiveness of the composition in enhancing tropoelastin formation as well as for other reasons (e.g., composition stability, aesthetics, and the like). For example, the NFκB-inhibitor and tropoelastin promoter may be present in a concentration by weight ratio (which is determined by dividing the concentration by weight of the NFκB-inhibitor by the concentration by weight of the tropoelastin promoter) of about 0.001 to about 100, preferably about 0.01 to about 10, more preferably about 0.02 to about 2.

Topical Compositions

The compositions of the present invention are applied topically to human skin and/or hair. In addition to the NFκB-inhibitor and tropoelastin promoter, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically-acceptable topical carrier includes water. The cosmetically-acceptable topical carrier may include one or more ingredients selected from the group consisting of wetting agents, emollients, oils, humectants, and the like. In one embodiment, the cosmetically-acceptable topical carrier is or includes a substrate such as a non-woven fabric or film material.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to solutions, suspensions, emulsions such as microemulsions and nanoemulsions, gels, solids and liposomes.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Although it is preferred that the composition of the present invention includes water, the composition may alternatively be anhydrous or an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of suitable emulsifiers include those typically identified as such in the art of personal care and cosmetic formulations.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Active Agents

In one embodiment, the composition further contains another cosmetically active agent. As used herein, a "cosmetically active agent" is a compound (e.g., a synthetic compound or a compound isolated from a natural source or a natural extract) that has a cosmetic or therapeutic effect on the skin or hair, including, but not limiting to, anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for hair and/or skin conditioning.

In one embodiment, the agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, amines (e.g., neutrol), retinoids such as retinol and retinol palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides, amino acids such as proline, vitamins, lactobionic acid, acetyl-coenzyme A, niacin, riboflavin, thiamin, ribose, electron transporters such as NADH and FADH2, and other botanical extracts such as aloe vera, feverfew, oatmeal and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, vitamin B12, vitamin C, vitamin K, and different forms of vitamin E like alpha, beta, gamma or delta tocopherols or their mixtures, and derivatives thereof.

Examples of hydroxy acids include, but are not limited to, glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the composition, as known in the art. These include humectants, pH adjusters, chelating agents (e.g., EDTA), fragrances, and preservatives (e.g., parabens). Examples of such agents are listed in pp. 2922-23, 2926-28, and 2892 of the ICI Handbook.

Water or alcohol soluble dyes may also be suitable to use in compositions of the present invention. Examples of dyes suitable for the compositions of the invention include caramel, carmine, fluorescein derivatives, methoxsalen, trioxsalen, azo dyes, anthraquinone dyes, blue azulenes, guajazulene, chamuzulene, erythrosin, bengal rose, phloxin, cyanosin, daphinin, eosin G, cosin 10B, Acid Red 51, Red Dye 4, Red Dye 40, Blue Dye 1, and Yellow Dye 5, or mixtures thereof.

When used, the amount of dye in the composition may vary from about 0.0001 to about 0.1, preferably about 0.0025 to about 0.025, weight percent based on the total weight of the composition.

The composition and formulations and products containing such compositions of the present invention may be prepared using methodology that is well known by an artisan of ordinary skill.

Methods of Use

Compositions of the present invention may be topically applied to mammalian skin that is in need of treatment for one or more signs of skin aging as described above. In one embodiment, the compositions are applied to skin in need of treatment for lines and wrinkles and/or loss of elasticity. The compositions may be applied to the skin in need of such treatment according to a suitable treatment regimen, e.g., every month, every week, every other day, every day, twice a day, or the like.

In certain embodiments, compositions of the present invention may also be useful for treating other needs associated with skin. For example, compositions of the present invention may be useful for treating post-inflammatory hyperpigmentation, for reducing pore size, for reducing sebum production, and for scar mitigation. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mucosa or other tissue such as vaginal, oral, or ocular tissue. In certain other embodiments, compositions of the present invention are applied to mild wounds or post-surgical sites to facilitate healing, to insect bites, to poison ivy or similar skin conditions, or in general to mitigate itch.

According to the invention, the combination of an NFκB-inhibitor and a tropoelastin promoter provides an increased, preferably synergistic boost in tropoelastin promotion over that provided by either the NFκB-inhibitor or the tropoelastin promoter alone. For example, the combination may provide an increase in tropoelastin promotion as measured by the TROPOELASTIN PROMOTER ASSAY on the order of at least about 30-40%, preferably at least about 40-50%, more preferably greater than about 50%, over the tropoelastin promotion provided by the tropoelastin promoter alone.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

EXAMPLE 1

The NFκB-INHIBITION TEST described above was performed on test samples of Bay 11-7082 (Sigma-Aldrich, St. Louis, Mo.), Tetrahydrocurcuminoids CG (Sabinsa Corporation, Piscataway, N.J.), as well as various concentrations of 4-hexylresorcinol. The results are shown in Table 1, in which NF-kB Gene Reporter Activation (Luminescence, L) is reported for the test samples and a control sample. Percent NF-kB Inhibition is also reported.

TABLE 1

| | NF-kB Gene Reporter Activation (Luminescence, L) | Percent NF-kB Inhibition |
|---|---|---|
| Untreated | 1.2 ± 0.3 | — |
| TNFα (100 ng/ml) Stimulated, "$L_{control}$" | 108.2 ± 8.5 | — |

TABLE 1-continued

| | NF-kB Gene Reporter Activation (Luminescence, L) | Percent NF-kB Inhibition |
|---|---|---|
| TNFα + 4-Hexylresorcinol (50 ug/ml) | 9.3 ± 0.9 | 91.4% |
| TNFα + 4-Hexylresorcinol (10 ug/ml) | 29.3 ± 9.2 | 72.9% |
| TNFα + 4-Hexylresorcinol (5 ug/ml) | 55.1 ± 1.7 | 50.9% |
| TNFα + 4-Hexylresorcinol (1 ug/ml) | 106.1 ± 1.9 | 1.9% |
| TNFα + Tetrahydrocurcuminoids CG (10 ug/ml) | 37.8 ± 2.6 | 65.1% |
| Bay 11-7082 (25 uM) | 11.3 ± 5.6 | 89.5% |

Bay 11-7082 and Tetrahydrocurcuminoids CG showed strong NF-kB inhibition. Unexpectedly, 4-hexylresorcinol also resulted in a substantial reduction in NF-kB activation. Even more unexpectedly, 4-hexylresorcinol showed substantial NF-kB inhibition even at low concentrations.

EXAMPLE 2

The NFκB-INHIBITION TEST described above was performed on a series of substituted resorcinols each having a concentration of 10 ug/ml. The results are shown in Table 2.

TABLE 2

| | Structure | Percent NF-kB Inhibition |
|---|---|---|
| 4-Octylresorcinol | 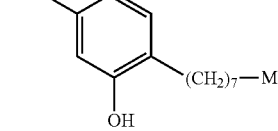 | 99.5% |
| 4-Hexylresorcinol | 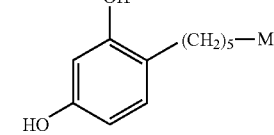 | 92.4% |
| β-Zearalenol CAS#71030-11-0 | 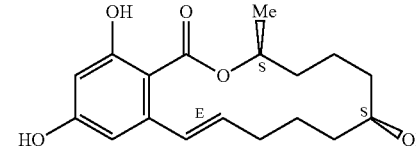 | 87.1% |
| β-Zearalanol CAS#42422-68-4 | 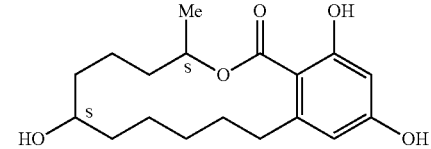 | 76.56% |
| 2,4-Dinitrosorcinol | 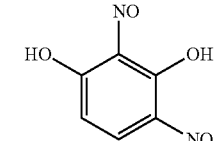 | 51.78% |
| 4-Chlororesorcinol | 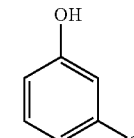 | 51.63% |
| 2,6-Dichlororesorcinol | 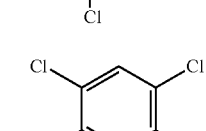 | 51.54% |

TABLE 2-continued

| Structure | Percent NF-kB Inhibition |
|---|---|
| Zearalanone | 50.95% |
| Phenethylresorcinol | 31.8% |
| 4-Dodecylresorcinol | 20.87% |
| 4-Caproylresorcinol | 10.25% |
| C-Undecylcalix[4]-resorcinarene | 4.87% |
| 3-Methoxyphenol | 0% |
| 2',4'-Dihydroxypropiophenone | −0.7% |
| 2,4-Dihydroxycinnamic Acid | −1.7% |

TABLE 2-continued

| | Structure | Percent NF-kB Inhibition |
|---|---|---|
| 1,3-Dimethoxybenzene | MeO—C6H4—OMe | −1.7% |

It can be seen from the data in Table 2 that superior NFκB inhibition is provided by substituted resorcinols containing only substituents free of phenyl functionalities, substituted resorcinols containing only substituents free of ketone functionalities, and substituted resorcinols comprising a substituent having 5 to 11 carbon atoms.

EXAMPLE 3

The TROPOELASTIN PROMOTER ASSAY was performed on the following compounds: *Tanacetum parthenium* (parthenolide-free feverfew extract from Integrated Botanical Technologies of Ossining, N.Y.), *Rubus fruticosus* (SymMatrix, from Symrise), cells treated with various preparations of *Phyllanthus niruri* (Raintree Nutrition, Inc., Carson City, Nev.) subsequently extracted with water and fractionated to include only species with molecular weight less than 100,000 daltons, and 4-hexylresorcinol (Synovea HR, Sytheon Ltd).

The compounds were diluted in cell culture media (DMEM Media of Invitrogen, San Diego Calif.) to the concentration of "active" indicated in Table 3 below. The compounds were added to the transfected H9C2 cells and were incubated for 24 hours. Test samples were compared to a DMSO vehicle.

The results are shown in Table 3.

combination of both 4-hexylresorcinol and *Tanacetum parthenium* demonstrated an 84% improvement in tropoelastin promotion over the vehicle control. This was much greater than a mere additive effect in performance.

A similar synergistic effect was observed when the concentration of *Tanacetum parthenium* was raised from 1 ug/ml to 5 ug/ml. *Tanacetum parthenium* at the higher concentration showed a percent change in tropoelastin promotion over the vehicle control of 59.3%, whereas the combination of 4-hexylresorcinol and *Tanacetum parthenium* achieved a percent change in tropoelastin promotion over the vehicle control of 115.8%.

Similarly, 4-hexylresorcinol and *Phyllanthus niruri* showed percent changes in tropoelastin promotion over the vehicle control of −12% and 18.9%, respectively. The combination of 4-hexylresorcinol and *Phyllanthus niruri* achieved a synergistic percent change in tropoelastin promotion over the vehicle control of 67.8%.

4-Hexylresorcinol and *Rubus fruticosus* showed percent changes in tropoelastin promotion over the vehicle control of −12% and 30.4%, respectively, whereas the combination of 4-hexylresorcinol and *Rubus fruticosus* achieved a percent change in tropoelastin promotion over the vehicle control of 77.3%. This was much greater what would be expected from a mere additive effect.

TABLE 3

| Compound/Extract | Respective Concentrations of Actives (on active basis) | Tropoelastin Promoter Activity | Percent Change Over Vehicle | Ratio of NFκB-Inhibitor:Tropoelastin Promoter |
|---|---|---|---|---|
| Vehicle Control (DMSO) | 0.01% | 1.36 ± 0.33 | — | |
| 4-Hexylresorcinol | 0.1 ug/ml | 1.2 ± 0.12 | −12% | |
| *Tanacetum parthenium* | 1 ug/ml | 1.54 ± .025 | 13.3% | |
| 4-Hexylresorcinol + *Tanacetum parthenium* | 0.1 ug/ml + 1 ug/ml | 2.51 ± .0.23* | 84.5% | 1:10 |
| *Tanacetum parthenium* | 5 ug/ml | 2.17 ± 0.18 | 59.3% | |
| 4-Hexylresorcinol + *Tanacetum parthenium* | 0.1 ug/ml + 5 ug/ml | 2.94 ± 0.38* | 115.8% | 1:50 |
| *Phyllanthus niruri* | 0.1 ug/ml | 1.62 ± 0.16 | 18.9% | |
| 4-Hexylresorcinol + *Phyllanthus niruri* | 0.1 ug/ml + 0.1 ug/ml | 2.29 ± 0.20* | 67.8% | 1:1 |
| *Rubus fruticosus* | 0.5 ug/ml | 1.33 ± 0.12 | 30.4% | |
| 4-Hexylresorcinol + *Rubus fruticosus* | 0.1 ug/ml + 0.5 ug/ml | 2.42 ± 0.18* | 77.3% | 1:5 |

*= P < 0.05 compared to compound/extract alone using a paired students t-Test

As can be seen from the results shown in Table 3, 4-hexylresorcinol and *Tanacetum parthenium* demonstrated percent changes in tropoelastin promotion over the vehicle control of −12% and 13.3%, respectively. In contrast, the Additional TROPOELASTIN PROMOTER ASSAYS demonstrated the synergistic effect of another NF-kB inhibitor, Tetrahydrocurcuminoids CG in combination with *Tanacetum parthenium*. The results are shown in Table 4 below.

TABLE 4

| Compound/Extract | Respective Concentrations of Actives (on active basis) | Tropoelastin Promoter Activity | Percent Change Over Vehicle | Ratio of NFκB-Inhibitor:Tropoelastin Promoter |
|---|---|---|---|---|
| Vehicle Control (DMSO) | 0.01% | 1.00 ± 0.13 | — | |
| Tetrahydrocurcuminoids CG | 10 ug/ml | 0.72 ± 0.15 | −28.0% | |
| Tanacetum parthenium | 5 ug/ml | 1.11 ± 0.23 | 11.4% | |
| Tetrahydrocurcuminoids CG + Tanacetum parthenium | 10 ug/ml + 5 ug/ml | 1.41 ± 0.20* | 41.4% | 2:1 |

*=P < 0.05 compared to compound/extract alone using a paired students t-Test

Tetrahydrocurcuminoids CG and *Tanacetum parthenium* showed percent changes in tropoelastin promotion over the vehicle control of −28% and 11.4% respectively, while the combination of Tetrahydrocurcuminoids CG and *Tanacetum parthenium* achieved a percent change in tropoelastin promotion over the vehicle control of 41.4%.

The data clearly demonstrates that the combination of an NF-KB inhibitor and a tropoelastin promoter produces a surprising and synergistic increase in tropoelastin promotion activity.

EXAMPLE 4

A composition according to the invention using the ingredients shown in Table 5 below was prepared.

TABLE 5

| INCI name | Trade name | Percentage |
|---|---|---|
| Deionized water | Purified water | 77% |
| Pentylene glycol | HYDROLITE 5 | 5% |
| Hexyl resorcinol | SYNOVEA HR | 1% |
| Oleosome | NATRULON OSF oleosomes | 10% |
| C12-15 Alkyl Benzoate | FINSOLV TN | 4% |
| Ammonium Acryloyldimethyl-taurate/VP Copolymer | ARISTOFLEX AVC | 2% |
| Chrysanthemum Parthenium (Feverfew) Leaf/Flower/Stem Juice | Tanacetum parthenium extract | 1% |

FINSOLV TN is available from Finetex, Inc. of Elmwood Park, NJ
HYDROLITE 5 is available from Symrise of Teterboro, NJ
SYNOVEA HR is available from Sytheon of Lincoln Park, NJ
ARISTOFLEX AVC is available from Clariant of Frankfurt, Germany
NATRULON OSF oleosomes from Lonza of Allendale, NJ The composition was prepared by the following method. The Synovea HR was weighed and dissolved in HYDROLITE 5 and deionized water was added to form Phase A. Oleosomes and Finsolv TN were mixed to form Phase B. Phase B was added to Phase A very slowly under continuous mixing. Mixing was continued for 15 minutes until a uniform emulsion was formed. ARISTOFLEX was added to the emulsion under continuous mixing at high speed to obtain a thick, smooth and homogenous formulation.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

The invention claimed is:

1. A composition comprising:
    an NFκB-inhibitor selected from the group consisting of 4-hexyl resorcinol and tetrahydrocurcuminoids;
    a tropoelastin promoter selected from the group consisting of blackberry extracts and extracts of *Phyllanthus niruri*; and
    a cosmetically-acceptable topical carrier,
    wherein the composition is an emulsion and the concentration by weight ratio of the NFκB-inhibitor to tropoelastin promoter is about 0.001 to about 100.

2. The composition of claim 1, wherein the concentration by weight ratio of the NFκB-inhibitor to tropoelastin promoter is about 0.02 to about 2.

3. The composition of claim 1, wherein the tropoelastin promoter is a blackberry extract.

* * * * *